United States Patent [19]

Colclough et al.

[11] Patent Number: 5,703,262
[45] Date of Patent: Dec. 30, 1997

[54] PROCESS FOR THE PREPARATION OF DITHIOPHOSPHORIC ACIDS

[75] Inventors: Terence Colclough, Abingdon; Philip Skinner, Wantage; John Derek Woollins, London, all of United Kingdom; Paul Thomas Wood, Clemson, S.C.

[73] Assignee: Exxon Chemical Patents Inc, Linden, N.J.

[21] Appl. No.: 573,209

[22] PCT Filed: Jan. 9, 1990

[86] PCT No.: PCT/EP90/00055

§ 371 Date: Apr. 6, 1993

§ 102(e) Date: Apr. 6, 1993

[87] PCT Pub. No.: WO90/07512

PCT Pub. Date: Jul. 12, 1990

[51] Int. Cl.$^6$ .................. C07F 9/18; C07F 9/17; C07F 9/165
[52] U.S. Cl. .................. 558/112; 558/123
[58] Field of Search .................. 558/123, 112

[56] References Cited

U.S. PATENT DOCUMENTS 3,274,300  9/1966  Wazer et al. .................. 558/70

*Primary Examiner*—Michael G. Ambrose
*Attorney, Agent, or Firm*—Estelle C. Bakun

[57] ABSTRACT

Dithiophosphoric acids are advantageously produced by reaction of an alcohol or phenol with phosphorus sesquisulphide in the presence of sulphur, preferably at the reflux temperature of the alcohol used.

4 Claims, No Drawings

PROCESS FOR THE PREPARATION OF DITHIOPHOSPHORIC ACIDS

This invention relates to the preparation of dithiophosphoric acids.

Dithiophosphoric acids, which are important intermediates in the production of lubricant and oil additives, are generally made by reaction of phosphorus(V) sulphide (also called tetraphosphorus decasulphide, $P_4S_{10}$) with an appropriate alcohol or phenol. The reaction proceeds in accordance with the equation:

$$P_4S_{10} + 8ROH \rightarrow 4(RO)_2PS_2H + 2H_2S$$

where ROH is the alcohol or phenol.

According to U.S. Pat. No. 3,274,300 (Van Wazer et al) improved yields of dialkyldithiophosphoric acids (called in this specification O,O-dialkylphosphorodithioates) are obtained if the alcohol is reacted with a phosphorus sulphide and an excess of sulphur. According to this specification, it is essential to use sufficient sulphur to provide a sulphur to phosphorus atomic ratio of at least 2.6, i.e. more sulphur than that required to form phosphorus(V) sulphide, and this excess sulphur must be in solution or chemical combination with the phosphorus in the phosphorus sulphide composition. A mechanical mixture of sulphur with phosphorus(V) sulphide gives an inferior result and according to a comparative example, reaction of phosphorus(V) sulphide with n-butanol at the reflux temperature (about 114° C.) in the presence of additional sulphur to provide an overall atomic ratio of sulphur to additional sulphur to provide an overall atomic ratio of sulphur to phosphorus of 3.5, gives a yield of dibutyldithiophosphoric acid (O,O-dibutylphosphorodithioate) of only about 60%.

We have now surprisingly discovered that excellent yields of dithiophosphoric acids may be obtained by reaction of phosphorus sesquisulphide ($P_4S_3$) with elemental sulphur and the required alcohol or phenol at elevated temperature. The reaction apparently proceeds in accordance with the equation:

$$P_4S_3 + \tfrac{7}{8}S_8 + 8ROH \rightarrow 4(RO)_2PS_2H + 2H_2S$$

(where ROH is the alcohol or phenol used). This reaction has the same overall stoichiometry as the reaction of phosphorus (V) sulphide with an alcohol, but it is totally unexpected that phosphorus sesquisulphide would react with sulphur at the relatively low temperatures which are used in the new process, and indeed it is not clear that the new process proceeds via phosphorus(V) sulphide as intermediate.

The present invention accordingly provides a process for the preparation of a dithiophosphoric acid which comprises reacting phosphorus sesquisulphide with sulphur and an alcohol or phenol at elevated temperature, the overall atomic ratio of sulphur to phosphorus being at least 2.5 to 1.

The process is preferably performed at a temperature from about 85° C. to 150° C., and most conveniently at the reflux temperature of the alcohol or phenol used. A solvent may be included in the reaction mixture, but is usually unnecessary unless the boiling point of the alcohol or phenol used is above the decomposition temperature of the starting materials or reaction products.

A wide variety of alcohols or phenols can be used in the new process including more particularly mono- and polyhydric, straight or branched aliphatic alcohols of up to 20, preferably 3 to 10, carbon atoms, which may be substituted, eg. by a mercapto radical of formula R'-S- where R' is a substituted or unsubstituted aliphatic radical of up to 12 carbon atoms or by an acyloxy radical of up to 20 carbon atoms, and alkyphenols having up to 20 carbon atoms in the alkyl residue. Specific examples of alcohol and phenols which can be used in the new process are n-butanol, 2-ethylhexan-1-ol, isobutanol, glycerol, glycerylmonooleate, p-nonyl-phenol and p-dodecylphenol. Mixtures of alcohols and phenols can also be used, eg. isopropanol and sec-hexanol, sec-butanol and iso-butanol, sec-butanol and 2-ethyl-hexanol, and isobutanol and isopentanol. Since for practical reasons a liquid product may be preferable to a solid crystalline product, use of mixtures of alcohols and/or phenols is often preferred.

The proportion of sulphur in relation to the phosphorus sesquisulphide should be at least sufficient for the stoichiometry of the reaction as set out above. Both the phosphorus sesquisulphide and the sulphur can be of ordinary reagent grade and in finely divided form.

Dithiophosphoric acids may be reacted with basic zinc compounds to form the corresponding zinc dihydrocarbyldithiophosphates which are well known lubricant additives, employed primarily as anti-wear agents but also providing anti-oxidant activity. The preparation of such zinc dithiophosphates and their use in lubricating oil compositions is well known to those skilled in the art.

The lubricating oil to which the metal dithiophosphate can be added includes mineral lubricating oils and synthetic lubricating oils and mixtures thereof. The synthetic oils include polyalphaolefins, diester oils such as di(2-ethylhexyl) sebacate, azelate and adipate, complex ester oils such as those formed from dicarboxylic acids, glycols and either monobasic acids or monohydric alcohols and silicone oils.

The lubricating oil base stock for the antioxidant additives of the present invention typically is adapted to perform a selected function by the incorporation of one or more additives therein to form lubricating oil compositions (i.e. formulations).

Representative additives typically present in such formulations include viscosity modifiers, corrosion inhibitors, other oxidation inhibitors, other friction modifiers, dispersants, anti-foaming agents, anti-wear agents, pour point depressants, detergents and rust inhibitors.

Viscosity modifiers impart high and low temperature operability to the lubricating oil and permit it to remain shear stable at elevated temperatures and also exhibit acceptable viscosity or fluidity at low temperatures.

Viscosity modifiers are generally high molecular weight hydrocarbon polymers including polyesters. The viscosity modifiers may also be derivatized to include other properties or functions, such as the addition of dispersancy properties.

These oil soluble viscosity modifying polymers will generally have number average molecular weights of from $10^3$ to $10^6$, preferably $10^4$ to $10^6$, e.g., 20,000 to 250,000, as determined by gel permeation chromatography or membrane osmometry.

Representative examples of suitable viscosity modifiers are any of the types known to the art including polisobutylene, copolymers of ethylene and propylene, polymethacrylates, methacrylate copolymers, copolymers of an unsaturated dicarboxylic acid and vinyl compound, interpolymers of styrene and acrylic esters, and styrene/isoprene copolymers.

Corrosion inhibitors, also known as anti-corrosive agents, reduce the degradation of the metallic parts contacted by the lubricating oil composition. Illustrative of corrosion inhibitors are phosphosulphurized hydrocarbons and the products obtained by reaction of a phosphosulphurized hydrocarbon with an alkaline earth metal oxide or hydroxide, preferably in the presence of an alkylated phenol or of an alkyphenol thioester, and also preferably in the presence of carbon dioxide. Phosphosulphurized hydrocarbons are prepared by reacting a suitable hydrocarbon such as terpene, a heavy petroleum fraction of a $C_2$ to $C_6$ olefin polymer such as polyisobutylene, with from 5 to 30 wt. % of a sulfide of phosphorus for ½ to 15 hours, at a temperature in the range of 150° to 600° F. Neutralization of the phosphosulphurized hydrocarbon may be effected in the manner taught in U.S. Pat. No. 1,969,324.

Oxidation inhibitors reduce the tendency of mineral oils to deteriorate in service which deterioation can be evidenced by the products of oxidation such as sludge and varnish-like deposits on the metal surfaces and by viscosity growth. Such oxidation inhibitors include ZDDP's, aromatic amines such as alkylated diphenylamines and phenyl alpha naphthylamine, hindered phenols, copper compounds, alkaline earth metal salts of alkylphenolthioesters having preferably $C_5$ to $C_{12}$ alkyl side chains, eg, calcium nonylphenol sulphide, barium t-octylphenyl sulphide, dioctylphenylamine, phenylalphanaphthylamine, phosphosulphurized or sulphurized hydrocarbons, etc.

Friction modifiers serve to impart the proper friction characteristics to lubricating oil compositions such as automatic transmission fluids.

Representative examples of suitable friction modifiers are found in U.S. Pat. No. 3,933,659 which discloses fatty acid esters and amides; U.S. Pat. No. 4,176,074 which describes molybdenum complexes of polyisobutenyl succinic anhydride-amino alkanols; U.S. Pat. No. 4,105,571 which discloses glycerol esters of dimerized fatty acids; U.S. Pat. No. 3,779,928 which discloses alkane phosphonic acid salts; U.S. Pat. No. 3,778,375 which discloses reaction products of a phosphonate with an oleamide; U.S. Pat. No. 3,852,205 which discloses S-carboxyalkylene hydrocarbyl succinimide, s-carboxyalkylene hydrocarbyl succinamic acid and mixtures thereof; U.S. Pat. No. 3,879,306, which discloses N-(hydroxyalkyl)alkenyl-succinamic acids or succinimides; U.S. Pat. No. 3,932,290, which discloses reaction products of di-(lower alkyl) phosphites and epoxides; and U.S. Pat. No. 4,028,258 which discloses the alkylene oxide adduct of phosphosulphurized N-(hydroxyalkyl) alkenyl succinimides. The most preferred friction modifiers are succinate esters, or metal salts thereof, of hydrocarbyl substituted succinic acids or anhydrides and thiobis alkanols such as described in U.S. Pat. No. 4,344,853.

Dispersants maintain oil insolubles, resulting from oxidation during use, in suspension in the fluid thus preventing sludge flocculation and precipitation or deposition on metal parts. Suitable dispersants include high molecular weight alkenyl succinimides, the reaction product of oil-soluble polyisobutylene succinic anhydride with ethylene amines such as tetraethylene pentamine and borated salts thereof.

Pour point depressants lower the temperature at which the fluid will flow or can be poured. Such depressants are well known. Typically of those additives which usefully optimize the low temperature fluidity of the fluid are $C_8$-$C_{18}$ dialkylfumarate vinyl acetate copolymers, polymethacrylates, and wax naphthalene. Foam control can be provided by an antifoamant of the polysiloxane type, eg, silicone oil and polydimethyl siloxane.

Detergents and metal rust inhibitors include the metal salts of sulphonic acids, alkyl phenols, sulphurized alkyl phenols, alkyl saliscylates, naphthenates and other oil soluble mono- and di-carboxylic acids.

Highly basic (viz, overbased) metals salts, such as highly basic alkaline earth metal sulphonates (especially Ca and Mg salts) are frequently used as detergents.

Copper and lead corrosion inhibitors and antiwear agents include borate esters, thiadiazoles such as derivatives of 2, 5 dimercapto 1,3,4-thiadiazole and benzotriazoles.

Some of these numerous additives can provide a multiplicity of effects, eg a dispersant-oxidation inhibitor. This approach is well known and need not be further elaborated herein.

Compositions when containing these conventional additives are typically blended into the base oil in amounts which are effective to provide their normal attendant function. Representative effective amounts of such additives are illustrated as follows:

| Additive | Vol % | Wt % a.i. |
| --- | --- | --- |
| Viscosity Modifier | .01–4 | .01–4 |
| Corrosion Inhibitor | 0.01–1 | .01–1.5 |
| Oxidation Inhibitor | 0.01–1 | .01–1.5 |
| Dispersant | 0.1–7 | 0.1–8 |
| Pour Point Depressant | 0.01–1 | .01–1.5 |
| Anti-Foaming Agents | 0.001–0.1 | .001–0.15 |
| Anti-Wear Agents | 0.001–1 | .001–1.5 |
| Friction Modifiers | 0.01–1 | .01–1.5 |
| Detergents/Rust Inhibitors | .01–2.5 | .01–3 |
| Mineral Oil Base | Balance | Balance |

All of said weight percents expressed herein are based on active ingredient (a.i.) content of the additive, and/or upon the total weight of any additive-package, or formulation which will be the sum of the a.i. weight of each additive plus the weight of total oil or diluent.

The amount of the mixture of dithiophosphate added to the lubricating oil is a minor proportion by weight, preferably less than 20% by weight, more preferably 0.2 to 2.0 and especially 0.5 to 1.5% by weight.

Additives for lubricating oils are generally supplied as concentrates in solvent (eg oil) for incorporation into the bulk lubricant. According to this invention a concentrate comprises a solvent and 20 to 90 weight % of the metal dithiophosphate of this invention. Suitable solvents include kerosene, aromatic naphthas, mineral lubricating oils etc. Such concentrates may contain one or more other lubricant additives such as described above to form a package which may be diluted with lubricant basestock to form a lubricating oil composition.

The following example illustrates the invention.

EXAMPLE

Phosphorus sesquisulphide (3.0 g, 13.6 m.mole) and sulphur (3.06 g, 11.9 m.mole) were heated in refluxing n-butanol (8.9 g, 120 m.mole) for 2 hours at 110° C. Hydrogen sulphide was evolved and the sulphur slowly dissolved. Analysis of the product by $^{31}P$ NMR showed that the yield of the expected O,O-dibutyldithiophosphate was 92% based on the phosphorus content.

If desired, the product may be separated from the excess n-butanol in known manner, e.g. by fractional distillation.

We claim:

1. A process for preparing a dithiophosphoric acid of the formula $(RO)_2PS_2H$, wherein R is derived from an aliphatic alcohol or phenol, comprising preparing a reaction mixture containing phosphorus sesquisulphide, sulphur, and one or more aliphatic alcohol or phenol wherein the overall atomic ratio of sulphur to phosphorus is at least 2.5 to 1, and refluxing the mixture at a temperature in the range of 85° to 150° C.

2. The process according to claim 1 in which the alcohol is a nonhydric or polyhydric straight or branched aliphatic alcohol of 3 to 10 carbon atoms, or an alkyl phenol having up to 20 carbon atoms in the alkyl residue.

3. The process according to claim 2 in which the alcohol is n-butanol or 2-ethylhexan-1-ol.

4. The process according to claim 2 or 3 in which the reaction is effected at the reflux temperature of the alcohol used.

* * * * *

UNITED STATES PATENT AND TRADEMARK OFFICE
CERTIFICATE OF CORRECTION

PATENT NO. : 5,703,262
DATED : December 30, 1997
INVENTOR(S) : T. Colclough et al.

It is certified that error appears in the above—identified patent and that said Letters Patent is hereby corrected as shown below:

In line 2 of claim 2, at column 4, line 67, delete "nonhydric" and insert therefor "monohydric".

Signed and Sealed this

Twenty-first Day of April, 1998

Attest:

BRUCE LEHMAN

Attesting Officer          Commissioner of Patents and Trademarks